(12) United States Patent
Park et al.

(10) Patent No.: US 10,245,337 B2
(45) Date of Patent: Apr. 2, 2019

(54) MULTIFUNCTION LIGHT-EMITTING DIODE LIGHTING APPARATUS

(71) Applicant: Seoul Viosys Co., Ltd., Ansan-si (KR)

(72) Inventors: Jung Youl Park, Ansan-si (KR); Jong Rack Kim, Ansan-si (KR); Young Hwan Son, Ansan-si (KR); Seong Min Lee, Ansan-si (KR); Jae Seon Yi, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 61 days.

(21) Appl. No.: 14/436,830

(22) PCT Filed: Dec. 3, 2013

(86) PCT No.: PCT/KR2013/011128
§ 371 (c)(1),
(2) Date: Apr. 17, 2015

(87) PCT Pub. No.: WO2014/088298
PCT Pub. Date: Jun. 12, 2014

(65) Prior Publication Data
US 2016/0136312 A1 May 19, 2016

(30) Foreign Application Priority Data
Dec. 3, 2012 (KR) .................... 10-2012-0139152

(51) Int. Cl.
*A61L 9/20* (2006.01)
*A61L 2/10* (2006.01)
(Continued)

(52) U.S. Cl.
CPC ................ *A61L 2/10* (2013.01); *A61L 9/20* (2013.01); *F21V 3/06* (2018.02); *F21V 23/003* (2013.01);
(Continued)

(58) Field of Classification Search
CPC ............ A61L 2/10; A61L 9/20; F21V 3/0409; F21V 23/003; F21Y 2113/13
(Continued)

(56) References Cited

U.S. PATENT DOCUMENTS

2008/0245788 A1\* 10/2008 Choong ................ F24C 15/008
219/758
2008/0286146 A1 11/2008 Schroll
(Continued)

FOREIGN PATENT DOCUMENTS

CN 201445668 U 5/2010
JP 2003-287358 A 10/2003
(Continued)

OTHER PUBLICATIONS

Park, Hye Lyun, Authorized Officer, Korean Intellectual Property Office, International Search Report, PCT Application No. PCT/KR2013/011128, dated Mar. 4, 2014, 2 pages.
(Continued)

*Primary Examiner* — Karabi Guharay
*Assistant Examiner* — Jessica M Apenteng
(74) *Attorney, Agent, or Firm* — Perkins Coie LLP (57) ABSTRACT

The multifunction LED lighting apparatus of the present invention includes a least one lighting LED, at least one ultraviolet (UV) LED, a substrate configured to have the at least one lighting LED and the at least one UV LED mounted thereon, and a cover disposed to face the substrate at a specific interval and configured to cover the lighting LED and the UV LED. The at least one lighting LED and the at least one UV LED are integrally mounted on the substrate and configured to form a single module of a thin sheet form, and the cover is installed to cover and support the single module placed on the inside wall of an application.

19 Claims, 7 Drawing Sheets

(51) Int. Cl.
  *F21V 33/00*         (2006.01)
  *F25D 27/00*         (2006.01)
  *F21V 23/00*         (2015.01)
  *F21V 23/04*         (2006.01)
  *F21V 3/06*          (2018.01)
  *F21W 131/305*       (2006.01)
  *F21Y 115/10*        (2016.01)
  *F21Y 113/13*        (2016.01)

(52) U.S. Cl.
  CPC .......... *F21V 23/04* (2013.01); *F21V 33/0044* (2013.01); *F21V 33/0064* (2013.01); *F25D 27/00* (2013.01); *F21W 2131/305* (2013.01); *F21Y 2113/13* (2016.08); *F21Y 2115/10* (2016.08)

(58) Field of Classification Search
  USPC .......................................................... 362/231
  See application file for complete search history.

(56) References Cited

U.S. PATENT DOCUMENTS

2011/0256019 A1* 10/2011 Gruen .................. A61L 2/10
                                                        422/24
2011/0286210 A1   11/2011 Shiue
2012/0199005 A1*  8/2012 Koji .................. A61L 9/205
                                                        96/224
2012/0262906 A1   10/2012 Wimbert
2012/0281418 A1*  11/2012 Eckert ................ F21V 7/0083
                                                        362/306
2013/0015753 A1*  1/2013 Son ..................... F25D 29/00
                                                        312/405
2014/0299793 A1*  10/2014 Deng ................... A61L 2/10
                                                        250/504 R

FOREIGN PATENT DOCUMENTS

| | | |
|---|---|---|
| JP | 2007003022 | 1/2007 |
| KR | 1020050045043 | 5/2005 |
| KR | 1020070045482 A | 5/2007 |

OTHER PUBLICATIONS

Second Office Action in Chinese Patent Application No. 201380060914.0, dated Jun. 1, 2018.

English translation of Korean Office Action from corresponding Korean Patent Application No. 10-2012-0139152 dated Dec. 26, 2018 (5 pages).

* cited by examiner

MULTIFUNCTION LIGHT-EMITTING DIODE LIGHTING APPARATUS

CROSS REFERENCE TO RELATED APPLICATION

This patent document is a 35 U.S.C. § 371 National Stage application of and claims the benefits and priority of PCT Application No. PCT/KR2013/011128, filed on Dec. 3, 2013, which further claims the benefits and priority of prior Korean Patent Application No. 10-2012-0139152, filed on Dec. 3, 2012. The entire disclosures of the above applications are incorporated by reference in their entirety as part of this document.

TECHNICAL FIELD

The present invention relates to a multifunction Light-Emitting Diode (LED) lighting apparatus, and more particularly, to a multifunction LED lighting apparatus which is capable of increasing the internal volume of an application on which the lighting apparatus is mounted by improving a structure in which a lighting apparatus having a sterilization and deodorization function is installed and of providing a high sterilization and deodorization function as an indoor lighting apparatus.

BACKGROUND ART

An LED is used as lighting means or display means that replaces an existing electric bulb because it have some advantages in that the size is small, consumption power versus brightness is high, lifespan is long, and a manufacturing cost is low.

An LED may be classified into an infrared LED that emits infrared rays, a visible ray LED that emits a visible ray, and an ultraviolet (UV) LED that emits ultraviolet rays depending on emission characteristics. After an UV LED was revealed to be effective in removing bacteria having DNA or RNA, the UV LED is used as a high-efficiency sterilization device which is cheap and easily used in various fields.

For example, some UV LEDs are installed in the interior of products, such as a home refrigerator, a warehouse refrigerator, a refrigerator mounted on a vehicle, a gimchi refrigerator, a cup sterilizer, and a shoes deodorizer, and used as sterilization devices for removing bacteria and smell. An example of a product which uses a conventional UV LED is disclosed in Korean Patent Laid-Open Publication No. 10-2010-0001915.

However, the product using the conventional UV LED is disadvantageous in that volume within the product is reduced because the product must be designed to provide an additional space within the product in order to install the UV LED.

Furthermore, a sterilization device using a UV LED requires additional electrical and electronic devices in order to configure an internal circuit for the sterilization device because the sterilization device is formed of an additional module. In such a case, a sterilization device using a conventional UV LED has a disadvantage in that volume within the sterilization device is reduced because an additional space on which electrical and electronic devices are mounted needs to be provided.

Furthermore, a sterilization device using a conventional UV LED has a disadvantage in that UV sterilization efficiency is deteriorated because a component that deteriorates UV light transmittance is added between a UV light source and a subject for photography in order to protect the UV light source or improve an external appearance of the sterilization device.

PRIOR ART DOCUMENT

Patent Document (Patent Document 0001) Korean Patent Laid-Open Publication No. 10-2010-0001915 (Jan. 6, 2010)

DISCLOSURE OF INVENTION

Technical Problem

Accordingly, the present invention has been made in an effort to solve the problems occurring in the related art, and an object of the present invention is to provide a multifunction LED lighting apparatus capable of substantially increasing the internal volume of a product on which the lighting apparatus is mounted by improving the structure of the lighting apparatus having a sterilization and deodorization function.

Another object of the present invention is to provide a multifunction LED lighting apparatus having a high sterilization and deodorization function, which may be used as an indoor lighting apparatus by improving the structure of the lighting apparatus having sterilization and deodorization function.

Solution to Problem

According to one aspect of the present invention, there is provided a multifunction LED lighting apparatus, including a least one lighting LED, at least one ultraviolet (UV) LED, a substrate configured to have the at least one lighting LED and the at least one UV LED mounted thereon, and a cover disposed to face the substrate at a specific interval and configured to cover the lighting LED and the UV LED. The at least one lighting LED and the at least one UV LED are integrally mounted on the substrate and configured to form a single module of a thin sheet form, and the cover is installed to cover and support the single module placed on the inside wall of an application.

In the multifunction LED lighting apparatus in accordance with an embodiment of the present invention, the substrate is inserted into a groove formed in the inside wall of the application.

In a multifunction LED lighting apparatus in accordance with another embodiment of the present invention, the UV LED is installed in the place where the UV LED radiates ultraviolet rays to a fluid, supplied to the interior of the application and discharged from a discharge port formed in the inside wall of the interior, when the fluid is discharged from the discharge port.

In a multifunction LED lighting apparatus in accordance with another embodiment of the present invention, the cover includes a partition configured to partition a first region facing the lighting LED and a second region facing the UV LED, and a light diffusion unit is included in the inner surface of the cover of the first region.

In a multifunction LED lighting apparatus in accordance with another embodiment of the present invention, the cover includes an opening unit formed in the second region facing the UV LED and configured to expose the UV LED to an outside of the cover.

A multifunction LED lighting apparatus in accordance with another embodiment of the present invention further includes a quartz member or a reinforced glass member for covering the opening unit.

A multifunction LED lighting apparatus in accordance with another embodiment of the present invention further includes a metal mesh cover for covering the opening unit. The metal mesh cover is coated with a photocatalyst.

In a multifunction LED lighting apparatus in accordance with another embodiment of the present invention, the cover includes an intake port connected to a discharge port configured to supply a fluid to the interior of the application, and a discharge port configured to discharge the fluid that passes from the intake port through a channel within the cover toward the interior space of an application.

In a multifunction LED lighting apparatus in accordance with another embodiment of the present invention, the cover further includes a photocatalyst coated on the inner surface of the channel.

In a multifunction LED lighting apparatus in accordance with another embodiment of the present invention, the UV LED includes a first UV LED installed in a first surface of the substrate and a second UV LED installed in a second surface of the substrate that faces the first surface.

In a multifunction LED lighting apparatus in accordance with another embodiment of the present invention, the first UV LED is disposed to face the cover, and the second UV LED is disposed to be exposed to a flow passage unit formed in the inside wall of the application.

In a multifunction LED lighting apparatus in accordance with another embodiment of the present invention, the first UV LED is disposed to face the cover, and the second UV LED is disposed to be exposed to a channel within a housing configured to cover the second UV LED and inserted into a groove formed in the inside wall of the application. The housing includes an intake port connected to the interior space of the application at one end of the channel and a discharge port connected to the interior space of the application formed at the other end of the channel.

A multifunction LED lighting apparatus in accordance with another embodiment of the present invention further includes a filter installed in the intake port.

A multifunction LED lighting apparatus in accordance with another embodiment of the present invention further includes a fan installed in at least any one of the intake port and the discharge port.

A multifunction LED lighting apparatus in accordance with another embodiment of the present invention further includes a photocatalyst coated on the inner surface of the channel.

In a multifunction LED lighting apparatus in accordance with another embodiment of the present invention, the application includes at least any one of a home refrigerator, a vehicle freezer, a warehouse refrigerator, a cup sterilizer, a toothbrush sterilizer, a shoes sterilization deodorizer, a fluid purification device, and a storage box.

According to still another aspect of the present invention, a multifunction LED lighting apparatus further includes a switch turned on or off in response to opening or shutting of a door of the application and a driving unit connected to the switch and configured to selectively drive the lighting LED and the UV LED in response to the on state and off state of the switch. The lighting LED, the UV LED, the substrate, and the driving unit are formed into a single module.

Advantageous Effects of Invention

By the features of the present invention, the multifunction LED lighting apparatus in accordance with the present invention is advantageous in that it can substantially increase the internal volume of a product on which the lighting apparatus is mounted by improving the structure of the lighting apparatus having a sterilization and deodorization function.

The multifunction LED lighting apparatus in accordance with an embodiment of the present invention is advantageous in that it can provide a high sterilization and deodorization function as the indoor lighting apparatus of an application by improving the structure of the lighting apparatus having sterilization and deodorization function.

The multifunction LED lighting apparatus in accordance with another embodiment of the present invention is advantageous in that it can provide a combination of a direct sterilization function and a sterilization and deodorization function using a photocatalyst in addition to a basic lighting function.

BRIEF DESCRIPTION OF DRAWINGS

The above objects, and other features and advantages of the present invention will become more apparent after a reading of the following detailed description taken in conjunction with the drawings, in which.

MODE FOR THE INVENTION

Terms or words used hereinafter should not be construed as having common or dictionary meanings, but should be construed as having meanings and concepts that comply with the technical spirit of the present invention on the basis of the principle that the inventor may appropriately define the concepts of the terms in order to best describe his or her invention. Accordingly, the following description and drawings illustrate exemplary embodiments of the present invention and do not fully represent the scope of the present invention. It would be understood by one of ordinary skill in the art that a variety of equivalents and modifications of the embodiments exist.

Terms used herein are used to describe specific embodiments and are not intended to limit the present invention. An expression of the singular number used in this specification may include an expression of the plural number unless clearly defined otherwise in the context.

Figure 1:
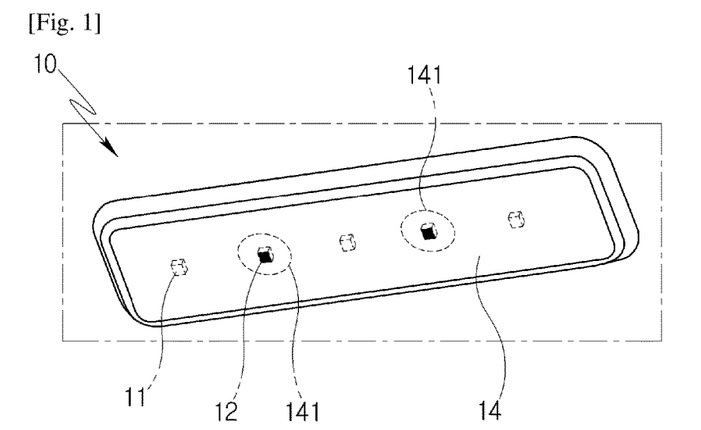
FIG. 1 is a schematic block diagram of a multifunction LED lighting apparatus in accordance with the present invention.
Figure 2:
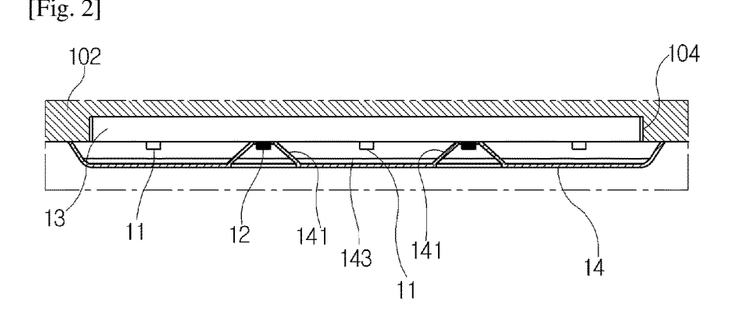
FIG. 2 is a lateral cross-sectional view of the multifunction LED lighting apparatus of FIG. 1.

FIG. 1 is a schematic block diagram of a multifunction LED lighting apparatus in accordance with the present invention, and FIG. 2 is a lateral cross-sectional view of the multifunction LED lighting apparatus of FIG. 1.

Referring to FIGS. 1 and 2, the multifunction LED lighting apparatus 10 in accordance with the present invention may include a lighting LED 11, an UV LED 12, a substrate 13, and a cover 14.

The lighting LED 11 refers to an LED produced so that it can be used as lighting. The lighting LED 11 may be made of III-V group material using a semiconductor process. The lighting LED 11 has a diode property, and the lighting LED 11 can be fabricated to emit light, such as red, green, yellow, or blue light, when an electric current is applied to the lighting LED 11. The lighting LED 11 may be fabricated to emit light white light using yellow phosphors in a blue LED.

The UV LED 12 refers an LED that radiates ultraviolet rays. Ultraviolet rays radiated from the UV LED 12 may have a wavelength of about 190~300 nm, more particularly, a wavelength of about 200~280 nm. In particular, it has been reported that ultraviolet rays having a wavelength of about 250~260 nm has great sterilizing power. For example, when ultraviolet rays having intensity of 100 μW per 1 $cm^2$ is radiated for 1 minute, about 99% of colon bacilli, diphtheria, and dysentery bacilli may be killed.

The lighting LED 11 and the UV LED 12 may be installed in a metal can or an ejection type lead frame package which can be mounted on the substrate 13, installed in the substrate 13 in such a way as to be subject to through hole mounting, or mounted on the substrate 13 in a bare chip type or a flip chip type. Furthermore, the UV LED 12 may be installed in such a way as to be attached to an intermediate substrate (i.e., submount) in order to improve a heat dissipation characteristic or electrical characteristics.

The substrate 13 refers to a base on which the lighting LED 11 and the UV LED 12 are mounted. The lighting LED 11 and the UV LED 12 mounted on the substrate 13 may be formed as single LED module of a thin sheet form.

The substrate 13 may be any one of a thermoelectric element, a plastic Printed Circuit Board (PCB) substrate, a ceramic substrate, and a metal substrate. In the present embodiment, a thermoelectric element may be made of thermoelectric materials in such a way as to operate as a cooling substrate for performing a cooling function by supplying only DC power to the thermoelectric element. If a thermoelectric element is used, one side of the thermoelectric element can be maintained as a cooling part up to −75° C., and thus the UV LED 12 can have an improved heat dissipation characteristic.

Furthermore, the substrate 13 may have one or more electrostatic protection circuits and output control circuits (corresponding to driving units) installed on at least one surface of the substrate 13 and may include coating materials coated or encapsulated on the substrate 13 in order to protect at least one of the electrostatic protection circuits and the output control circuits.

In the present embodiment, the substrate 13 is directly inserted into the groove 104 of the inside wall 102 of an application and mounted thereon. The application is a product in which the multifunction LED lighting apparatus in accordance with the present invention may be installed the interior space of the product. The application may include any one of a home refrigerator, a freezer mounted on a vehicle, a warehouse refrigerator, a cup sterilizer, a toothbrush sterilizer, a shoes sterilization deodorizer, a fluid purification device, and a storage box.

The cover 14 is disposed to face the substrate 13 at a specific interval and installed to cover the groove 104 into which the lighting LED 11, the UV LED 12, and the substrate 13 have been inserted. That is, the cover 14 is installed to cover and support a single module (i.e., LED module) installed on the inside wall of an application. The cover 14 can protect the LED module against the interior environment of the application and enables light or ultraviolet rays from the LED module to be properly radiated to the interior of the application.

Furthermore, the cover 14 includes an internal partition 141 that partitions a first region facing the lighting LED 11 and a second region facing the UV LED 12. The internal partition 141 may be integrally formed with the cover 14, for example, when the cover 14 is formed by ejection.

The cover 14 may further include a light diffusion unit 143 in the first region that faces the lighting LED 11. The light diffusion unit 143 functions to diffuse light emitted from the lighting LED 11 having strong straightness. The light diffusion unit 143 may be formed of a lens, a light diffusion agent, a light diffusion film, or a light diffusion plate and installed in the inner surface of the cover 14. When fabricating the cover 14, the light diffusion unit 143 may be fabricated to have a lens or concave-convex part structure in such a way as to perform a cover function and a light diffusion function and may be integrally formed with a cover member or coated or attached to the inner surface of the cover 14 by means of an additional member. The light diffusion unit 143 may be made of acrylic, polycarbonate, or polypropylene.

The multifunction LED lighting apparatus 10 in accordance with the present embodiment may include a driving unit (refer to 15 of FIG. 3) for driving the lighting LED 11 and the UV LED 12. The driving unit may be mounted on the substrate 13 along with the lighting LED 11 and the UV LED 12 or may be installed at another position of an application as an additional device depending on implementations.

Furthermore, the driving unit may be configured to selectively drive the lighting LED 11 and the UV LED 12 depending on an operation mode of an application or depending on whether a door is opened or not. In such a case, the driving unit may be connected to a switch (not shown) configured to be turned on or off depending on an operation mode of an application or depending on whether a door is opened or not.

In the present embodiment, the multifunction LED lighting apparatus 10 may be seated in the groove 104 that is installed in the inside wall 102 of the interior space of an application. In such a case, the multifunction LED lighting apparatus 10 is installed at a specific location (e.g., a location close to an outlet (refer to 107 of FIG. 9)) of the inside wall of an application for the purposes of a lighting function and a sterilization and deodorization function so that it can properly radiate ultraviolet rays in relation to a fluid output from a discharge port installed in the inside wall (e.g. 102) when the fluid supplied to the interior of the application is discharged from the discharge port.

Figure 3:
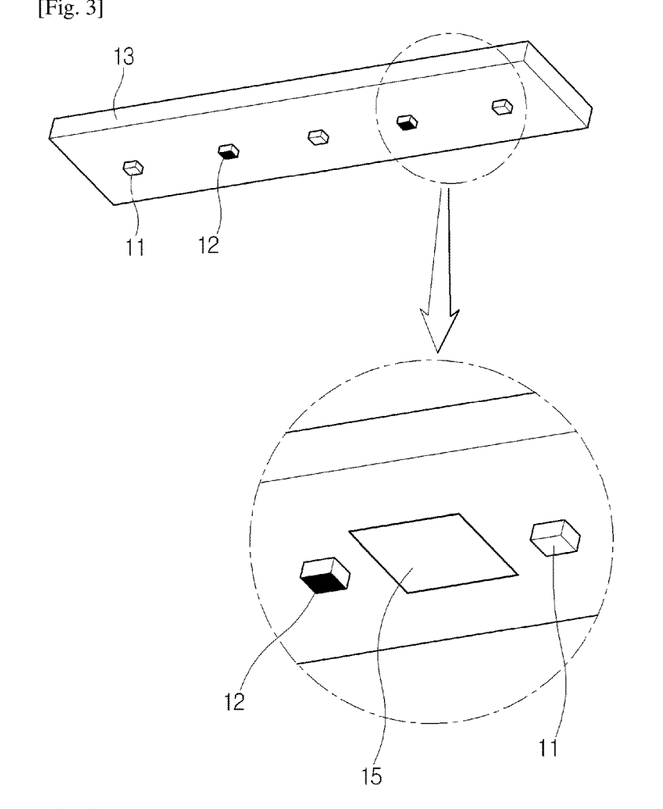
FIG. 3 is a partially enlarged perspective view of the LED module of the multifunction LED lighting apparatus shown in FIG. 2.

FIG. 3 is a partially enlarged perspective view of the LED module of the multifunction LED lighting apparatus shown in FIG. 2.

Referring to FIG. 3, the LED module in accordance with the present embodiment may include the substrate 13 and the lighting LED 11, the UV LED 12, and the driving unit 15 mounted on the substrate 13.

In the present embodiment, the driving unit 15 corresponds to an output control circuit for controlling driving voltage or a driving current supplied to the lighting LED 11 and the UV LED 12.

Figure 4:
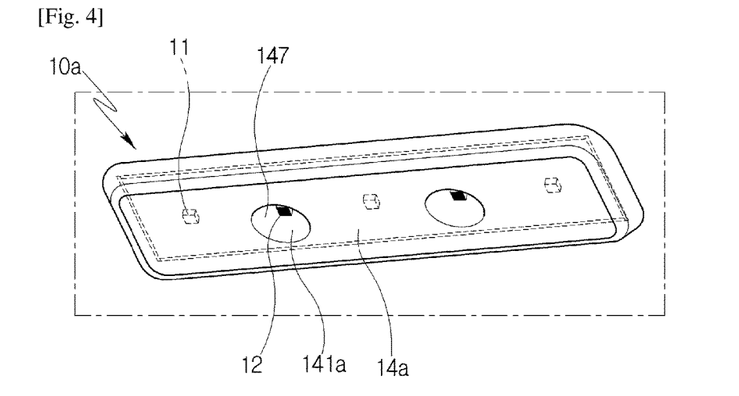
FIG. 4 is a perspective view of a multifunction LED lighting apparatus in accordance with an embodiment of the present invention.

FIG. 4 is a perspective view of a multifunction LED lighting apparatus in accordance with an embodiment of the present invention.

Referring to FIG. 4, the multifunction LED lighting apparatus 10a in accordance with an embodiment of the present invention may include a lighting LED 11, a UV LED 12, a substrate 13, and a cover 14a.

In the multifunction LED lighting apparatus 10a, the lighting LED 11, the UV LED 12, and the substrate 13 are substantially the same as those of the multifunction LED lighting apparatus 10 described with reference to FIGS. 1 and 2, and thus a detailed description thereof is omitted in order to avoid redundancy.

The cover 14a includes an opening unit 147 in a second region that faces the UV LED 12. In such a case, the UV LED 12 is partitioned from the lighting LED 11 by means of the opening unit 147 and a partition 141a placed within the opening unit 147 and exposed to the outside of the cover 14a.

The multifunction LED lighting apparatus 10a in accordance with the present embodiment can haven an improved sterilization effect because ultraviolet rays are directly radiated by the UV LED 12 that is directly exposed indoors.

In the present embodiment, the meaning that the UV LED 12 is directly exposed to the interior space of an application means that the UV LED 12 is not covered with the cover 14a. This means that the semiconductor layer of the UV LED or an electrode deposited on the semiconductor layer is not directly exposed to the interior space of an application.

Figure 5:
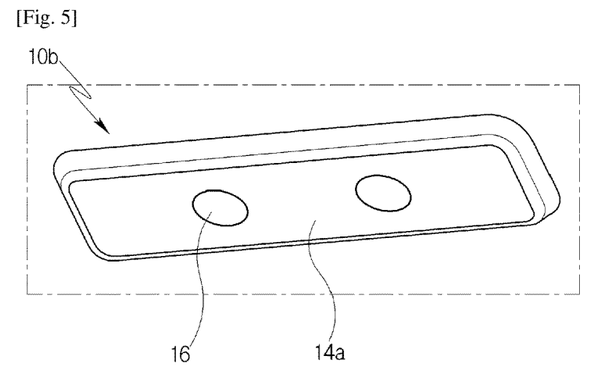
FIG. 5 is a perspective view of a multifunction LED lighting apparatus in accordance with another embodiment of the present invention.

FIG. 5 is a perspective view of a multifunction LED lighting apparatus in accordance with another embodiment of the present invention.

Referring to FIG. 5, the multifunction LED lighting apparatus 10b in accordance with another embodiment of the present invention may include a lighting LED 11, a UV LED 12, a substrate 13, a cover 14a, and finishing materials 16.

In the multifunction LED lighting apparatus 10b, the lighting LED 11, the UV LED 12, the substrate 13 and the cover 14a are substantially the same as those of the multifunction LED lighting apparatus 10a described with reference to FIG. 4, and thus a detailed description thereof is omitted in order to avoid redundancy.

The finishing materials 16 function to cover the opening unit (refer to 147 of FIG. 4) of the cover 14a. In the present embodiment, the finishing materials 16 may be formed of a quartz member or a reinforced glass member. The quartz member has UV transmittance of about 98% or more if UV is deep UV having a wavelength of 300 nm or less and thus functions to protect the UV LED 12 against the outside and also enables ultraviolet rays radiated from the UV LED 12 to be effectively transferred to the outside of the cover 14. Furthermore, the reinforced glass member has UV transmittance (based on a wavelength of 300 nm to 400 nm) of about 90% or more and thus functions to protect the UV LED 12 against the outside and also enables ultraviolet rays radiated from the UV LED 12 to be effectively radiated like the quartz member.

The multifunction LED lighting apparatus 10b in accordance with the present embodiment may have a slight smaller amount of ultraviolet rays than that of an UV LED that is directly exposed indoors, but can prevent the UV LED 12 from being damaged by an external shock.

Figure 6:
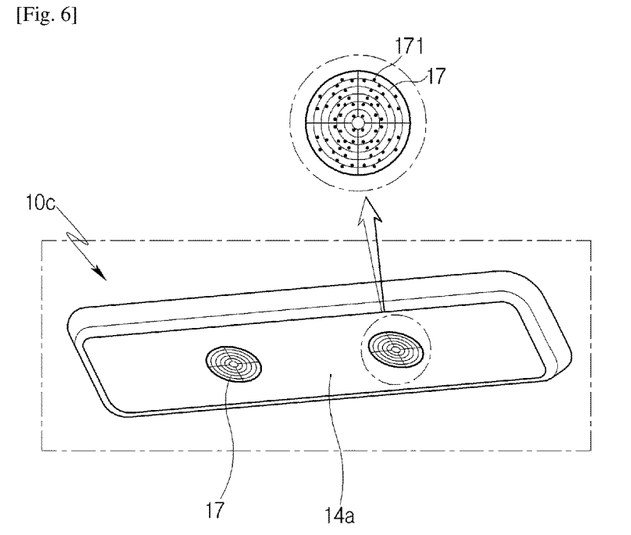
FIG. 6 is a perspective view of a multifunction LED lighting apparatus in accordance with another embodiment of the present invention.

FIG. 6 is a perspective view of a multifunction LED lighting apparatus in accordance with another embodiment of the present invention.

Referring to FIG. 6, the multifunction LED lighting apparatus 10c in accordance with another embodiment of the present invention may include a lighting LED 11, a UV LED 12, a substrate 13, a cover 14a, and a metal mesh cover 17.

In the multifunction LED lighting apparatus 10c, the lighting LED 11, the UV LED 12, the substrate 13, and the cover 14a are substantially the same as those of the multifunction LED lighting apparatus 10a described with reference to FIG. 4, and thus a detailed description thereof is omitted in order to avoid redundancy.

The metal mesh cover 17 includes finishing material shape that covers the opening unit (refer to 147 of FIG. 4) of the cover 14a. The metal mesh cover 17 functions to expose the UV LED 12 to the interior space of an application and also prevent an external object from the interior space from being inserted into the opening unit, thereby preventing damage to the UV LED 12. The metal mesh cover 17 may be made of materials which have a chemically resistant property and specific durability for an indoor environment depending on applications and do not block ultraviolet rays. For example, the metal mesh cover 17 may be a metal filter (or a metal foam) made of metal.

Furthermore, in the present embodiment, the metal mesh cover 17 may have a photocatalyst 171 coated on its surface. The photocatalyst 171 is activated by ultraviolet rays radiated from the UV LED 12, thus being capable of oxidizing and decomposing contaminants adsorbed to the metal mesh cover 17. The photocatalyst 171 may be any one or more selected from the group consisting of $TiO_2$, $SrTiO_3$, $WO_3$, $ZnO$, and a combination of them.

Figure 7:
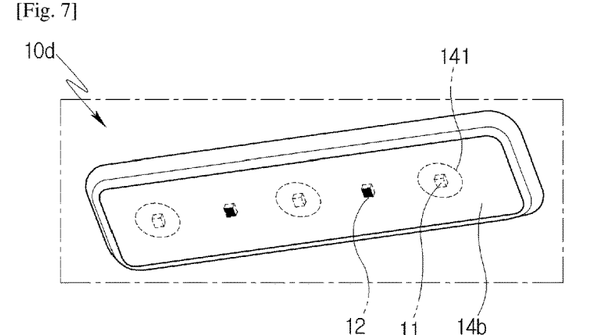
FIG. 7 is a perspective view of a multifunction LED lighting apparatus in accordance with another embodiment of the present invention.
Figure 8:
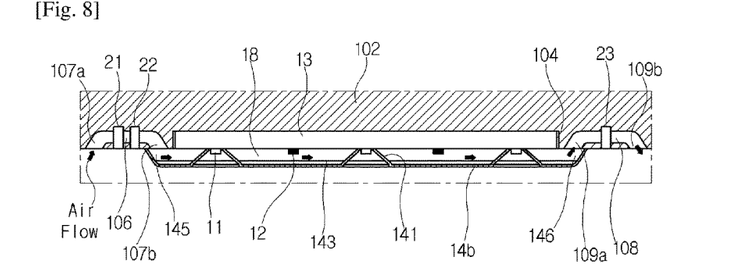
FIG. 8 is a cross-sectional view of the multifunction LED lighting apparatus of FIG. 7.
Figure 9:
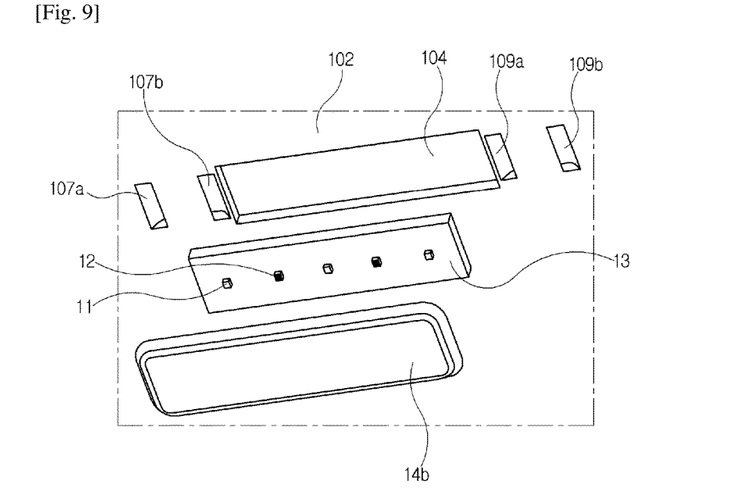
FIG. 9 is a partially exploded perspective view of the multifunction LED lighting apparatus of FIG. 8.

FIG. 7 is a perspective view of a multifunction LED lighting apparatus in accordance with yet another embodiment of the present invention, FIG. 8 is a cross-sectional view of the multifunction LED lighting apparatus of FIG. 7, and FIG. 9 is a partially exploded perspective view of the multifunction LED lighting apparatus of FIG. 8.

Referring to FIG. 7 to FIG. 9, the multifunction LED lighting apparatus 10d in accordance with another embodiment of the present invention may include a lighting LED 11, a UV LED 12, a substrate 13, and a cover 14b. In FIG. 8, the multifunction LED lighting apparatus 10d has been illustrated as being seated in the groove 104 of the inside wall 102 of an application.

In the multifunction LED lighting apparatus 10d, the lighting LED 11, the UV LED 12, and the substrate 13 are substantially the same as those of the multifunction LED lighting apparatus 10 described with reference to FIGS. 1 and 2, and thus a detailed description thereof is omitted in order to avoid redundancy.

The cover 14b is disposed to face the substrate 13 at a specific interval and to cover the lighting LED 11 and the UV LED 12. Furthermore, like in the aforementioned embodiment, the cover 14b may include an internal partition 141 configured to partition a first region facing the lighting LED 11 and a second region facing the UV LED 12. Here, a light diffusion unit 143 may be provided in the first region on the inner surface of the cover 14b that faces the lighting LED 11, and photocatalyst 171 may be coated on the second region on the inner surface of the cover 14b that faces the UV LED 12.

In the present embodiment, the cover 14b is disposed to further cover a portion that is extended from the edge of the groove 104 to the outside to some extent when the cover 14b covers the groove 104 of the inside wall 102 of the application. The second inflow hole 107b of a first flow passage unit 106 and the first outflow hole 109a of a second flow passage unit 108 are placed in the extended portion of the inside wall 102.

In accordance with the aforementioned construction, a fluid (e.g., air including contaminants) spread in the interior space of the application enters the first inflow hole 107a of the first flow passage unit 106 installed in the inside wall 102 of the application, exits from the second inflow hole 107b through the first flow passage unit 106, and enters the intake port 145 of the cover 14b connected to the second inflow hole 107b again. As a result, the fluid is discharged to the discharge port 146 of the cover 14b via the internal space 18 of the multifunction LED lighting apparatus 10d to which the UV LED 12 is exposed. Thereafter, the fluid enters the first outflow hole 109a of the second flow passage unit 108 connected to the discharge port 146, passes through the second flow passage unit 108, and exits from the second outflow hole 109b. As a result, the fluid is supplied to the interior space 18 again. That is, in accordance with the present embodiment, a fluid that is present in the interior space of an application can be sterilized and smell inherent in the fluid can be removed using the multifunction LED lighting apparatus installed as the indoor lighting apparatus of an application.

The multifunction LED lighting apparatus 10d in accordance with the present embodiment may further include fans 22 and 23 or a filter 21 on the flow path of a fluid in order to improve the removal efficiency of contaminants.

The filter 21 is disposed in the first flow passage unit 106 that is formed in the inside wall 102 of the application. The filter 21 functions to remove contaminants having relatively large volume within a fluid and thus supplies a fluid, including particles of a specific size or smaller, to the internal space 18 of the multifunction LED lighting apparatus 10d through the first flow passage unit 106.

For example, the filter 21 is a fluid purification filter and may be a metal filter made of metal. Furthermore, the metal filter may include a metal foam shape. The metal foam refers to porous foaming metal having the inside formed of a 3-D air bubble shape, and the metal foam may be made of metal, such as nickel, iron, chrome, or aluminum. Such metal foam is advantageous in that it has a large surface area per unit volume because it has a 3-D internal structure including a plurality of pores and it can be easily washed and used semipermanently.

The multifunction LED lighting apparatus 10d in accordance with the present embodiment may further include a catalyst or photocatalyst (refer to 171 of FIG. 6) coated on the filter 21. The catalyst may be made of materials (e.g., TiO2) which can oxidize and decompose contaminants adsorbed to the filter 21 through a reaction with ultraviolet rays.

The two fans 22 and 23 are disposed in the first flow passage unit 106 and the second flow passage unit 108, respectively, and are configured to form a flow of a fluid (e.g., a flow of air) that passes through the first flow passage unit 106, the internal space 18, and the second flow passage unit 108. Meanwhile, the fans are not limited to the aforementioned two fans, and the fan may be disposed only in the second flow passage unit 108, for example.

Furthermore, in the present embodiment, the number of UV LEDs 12 that radiate ultraviolet rays within the internal space 18 may be greater than that of UV LEDs described with reference to FIGS. 1 and 2, or the UV LEDs 12 may be densely installed at one place. The reason is as follows. Since the UV LED 12 in accordance with the present embodiment is disposed to radiate ultraviolet rays to a fluid that moves within the narrow internal space 18, the range in which the UV LED 12 radiates ultraviolet rays needs to substantially cover the entire cross section of at least specific section of the internal space 18 in order to improve a UV sterilization effect.

As described above, the multifunction LED lighting apparatus 10d in accordance with the present embodiment can be easily installed in such a manner that the LED module (corresponding to the substrate on which the lighting LED and the UV LED are mounted) is inserted into the groove 104 of the inside wall 102 of the application and the groove 104 is covered with the cover 14b as shown in FIG. 9. Furthermore, the multifunction LED lighting apparatus 10d can efficiently provide the interior lighting function of an application and the sterilization and/or deodorization function capable of removing bacteria within air when the air within the application flows through the internal space 18 using the flow passage units inserted into the inside wall of the application.

Figure 10:
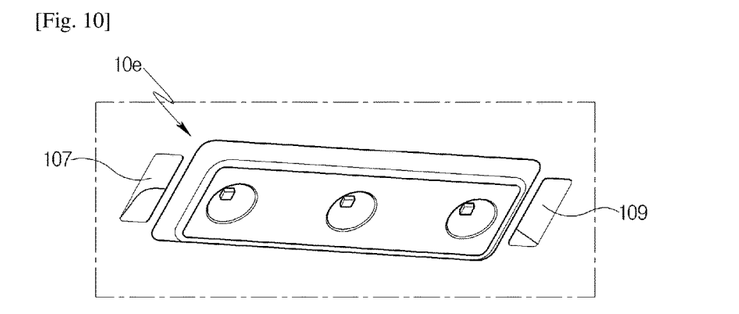
FIG. 10 is a perspective view of a multifunction LED lighting apparatus in accordance with another embodiment of the present invention.
Figure 11:
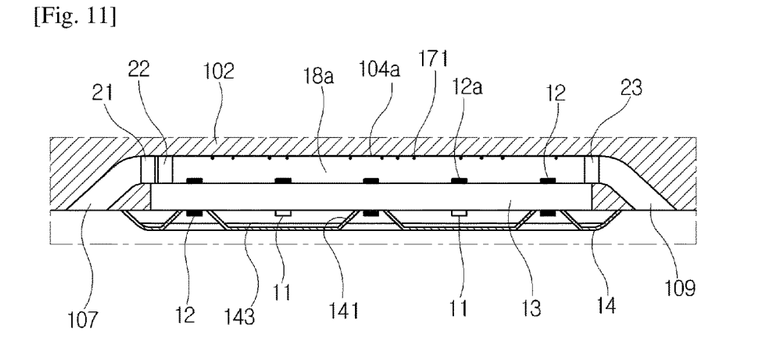
FIG. 11 is a cross-sectional view of the multifunction LED lighting apparatus of FIG. 10.

FIG. 10 is a perspective view of a multifunction LED lighting apparatus in accordance with yet another embodiment of the present invention, and FIG. 11 is a cross-sectional view of the multifunction LED lighting apparatus of FIG. 10.

Referring to FIG. 10 and FIG. 11, the multifunction LED lighting apparatus 10e in accordance with another embodiment of the present invention includes a lighting LED 11, a first UV LED 12, a second UV LED 12a, a substrate 13a, and a cover 14. In FIG. 11, the multifunction LED lighting apparatus 10e is seated in the groove of the inside wall 102 or the concave unit 104a of an application.

In the multifunction LED lighting apparatus 10e, the lighting LED 11, the first UV LED 12, and the cover 14 are substantially the same as those of the multifunction LED lighting apparatus 10 described with reference to FIGS. 1 and 2, and thus a detailed described thereof is omitted in order to avoid redundancy.

In the present embodiment, the first UV LED 12 may be installed in a first surface of the substrate 13a, and the second UV LED 12a may be installed in a second surface of the substrate 13a which faces the first surface of the substrate 13a. The second UV LED 12a is disposed to radiate ultraviolet rays toward the inside wall 102 of the application.

The multifunction LED lighting apparatus 10e in accordance with the present embodiment is seated in the groove or the concave unit 104a of the inside wall 102 of the application. In such a case, the multifunction LED lighting apparatus 10e may include a base (e.g., a casing or housing) which has a shape almost similar to the concave shape of a surface of the concave unit 104a. In other words, the multifunction LED lighting apparatus 10e may include a channel 18a connected to the interior space of the application in the internal space of the multifunction LED lighting apparatus 10e on one side and configured to form a fluid flow passage within the structure of the base. In such a case, the second UV LED 12a is disposed to radiate ultraviolet rays to the channel 18a. The number or an arrangement of second UV LEDs 12a may be set to radiate ultraviolet rays to the entire cross section of at least specific section of the channel 18a.

In order to improve sterilization and deodorization efficiency, the multifunction LED lighting apparatus 10e may further include a photocatalyst 171 coated on the inner surface of the channel 18a and configured to generate materials for controlling harmful components included in air when being activated by ultraviolet rays.

In accordance with the aforementioned multifunction LED lighting apparatus 10e, air that is present in the interior space of the application can be introduced into the channel 18a through an intake port 107 placed on one side of the channel 18a, sterilized by ultraviolet rays radiated from the second UV LED 12a, and then discharged to the interior space of the application through the discharge port 109 placed on the other side of the channel 18a.

The cover 14 in accordance with the present embodiment may be replaced with the cover 14a of any one of FIGS. 4 to 6 in addition to the cover structure of FIGS. 1 and 2. The cover 14 may include at least any one of the finishing materials 16, the metal mesh cover 17, and the photocatalyst 171 installed in the opening unit of the cover depending on implementations.

In the present embodiment, the multifunction LED lighting apparatus 10e has been illustrated as being partially inserted into the concave unit 104a of the inside wall of an application, but the present invention is not limited thereto. For example, the multifunction LED lighting apparatus 10e may have a structure in which a multifunction LED lighting apparatus having the channel 18a is attached to the flat inside wall (refer to 102) of an application depending on implementations. The channel 18a may include an outer flat surface corresponding to the flat inside wall (refer to 102).

Furthermore, like the aforementioned embodiment, the multifunction LED lighting apparatus 10e may include a filter 21 for filtering impurities of a specific size or greater within air introduced into the channel 18a and a first fan 22 or a second fan 23 or both for forming a forced air flow in the channel 18a.

In accordance with the present embodiment, the place where the multifunction LED lighting apparatus 10e is installed is not limited to a specific place of the inside wall 102 of an application, but the multifunction LED lighting apparatus 10e may be placed in a specific place of the inside wall of an application relatively freely so that it can perform a lighting function and a sterilization and deodorization function.

FIGS. 12 to 15 are diagrams showing applications which may adopt the multifunction LED lighting apparatus in accordance with the present invention.

Figure 12:
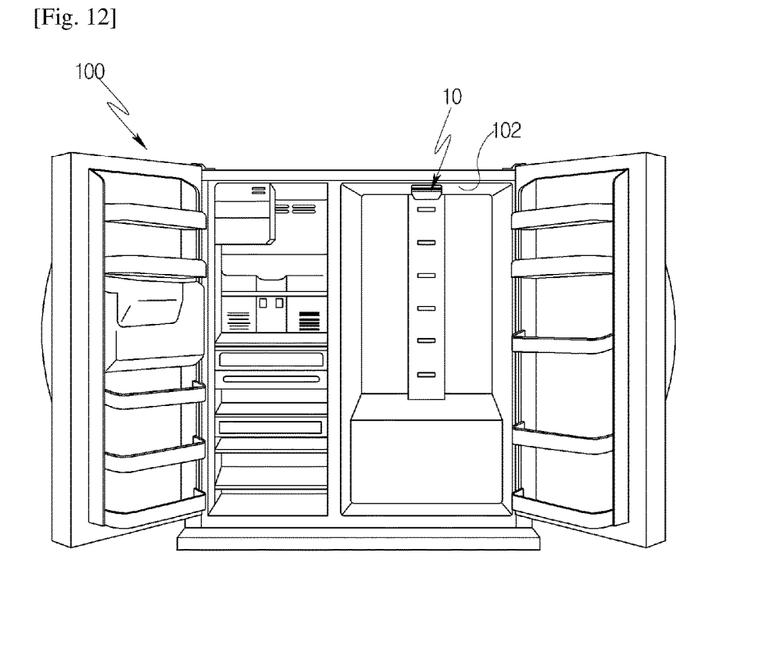
FIGS. 12 to 15 are diagrams showing products which may adopt the multifunction LED lighting apparatus in accordance with the present invention.

Referring to FIG. 12, the multifunction LED lighting apparatus 10 in accordance with the present invention may be adopted in a home refrigerator 100.

The home refrigerator 100 is an apparatus for keeping food at low temperature in order to prevent the decay or spoilage of the food and chiefly formed of a freezing room and a cooling room. A food keeping hygiene standard (EC) for a home refrigerator is 0~10 cfu/cm$^2$, which means that 10 bacteria or less are present per square centimeter when cultivating bacteria in a colony forming unit. It has been however reported that lots of bacteria are present in the home refrigerator 100. Researches carried out by Chon Jong-sik Research Team (Seoul National University of Korea) on April, 2012 revealed that bacteria present in the beverage chamber of a common home refrigerator was 7850 cfu/cm$^2$, which was much larger than average bacteria 5.4 cfu/cm$^2$ in the chamber pot of a toilet, the number of bacteria present in a mobile phone, or the number of bacteria present in the handle of a subway.

The multifunction LED lighting apparatus 10 in accordance with the present embodiment is inserted into a groove of the inside wall 102 of the refrigerator in such a manner than when the door of the refrigerator is opened, the UV LED is turned off and the lighting LED is turned on, thus radiating lighting to the inside of the refrigerator, and when the door of the refrigerator is closed, the lighting LED is turned off and the UV LED is turned on, thus sterilizing air within the refrigerator. Accordingly, the multifunction LED lighting apparatus 10 can be installed in such a way as not to reduce the capacity of the interior space of the home refrigerator 100 and can provide a lighting function and a sterilization and deodorization function. The effect in which the multifunction LED lighting apparatus 10 provides a lighting function and a sterilization and deodorization function while not substantially reducing the capacity of the interior space of the home refrigerator 100 is the same even in the multifunction LED lighting apparatuses 10a to 10e in accordance with other embodiments of the present invention.

Figure 13:
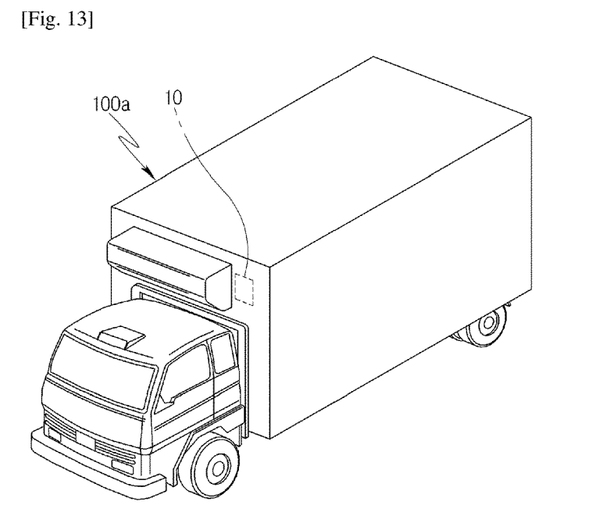
Figure 14:
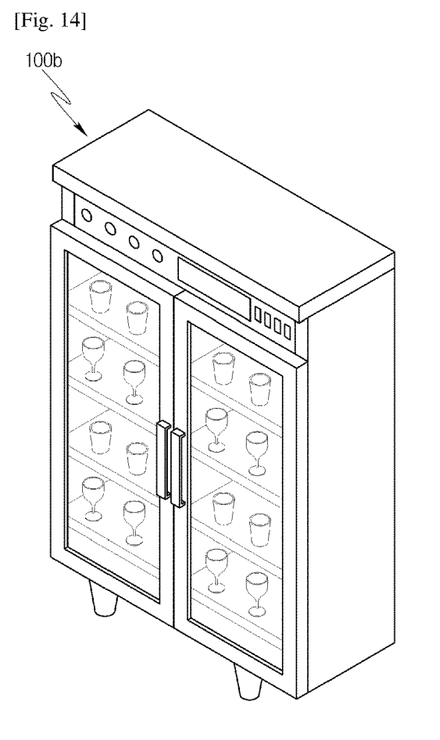
Figure 15:
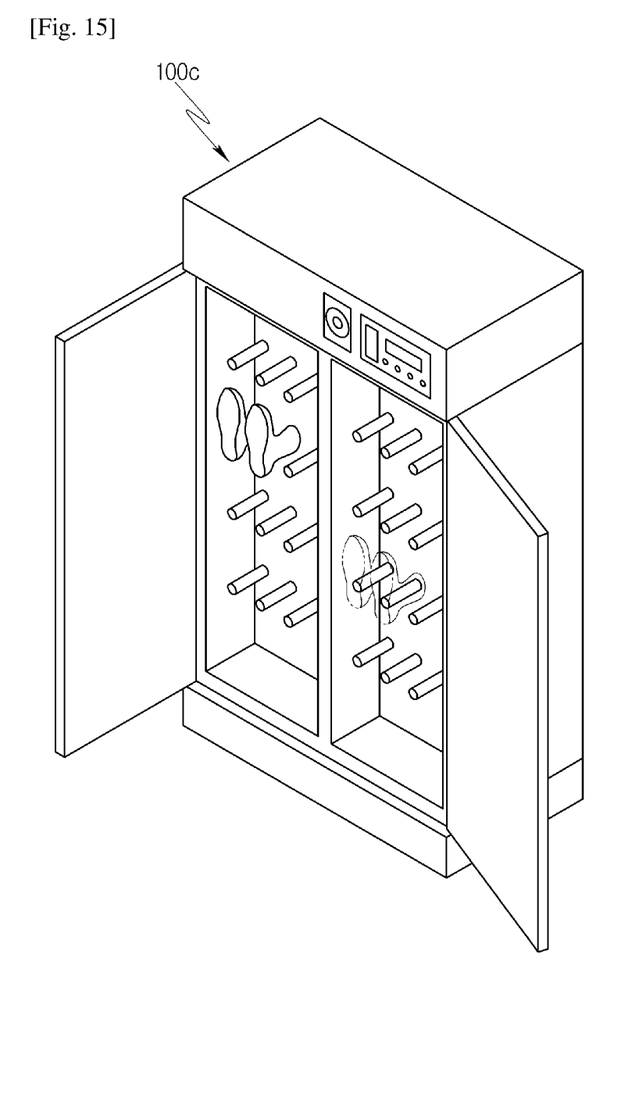

Referring to FIGS. 13 to 15, the multifunction LED lighting apparatus (any one of 10 and 10a to 10e) in accordance with the present invention may be adopted in a refrigerator 100a, a warehouse refrigerator (not shown), a cup drier 100b, a toothbrush sterilizer (not shown), a shoes sterilization deodorizer 100c, a fluid purification device (not shown), and other storage boxes (not shown).

The fluid purification device may include a casing configured to include an air flow passage provided between an intake port and a discharge port, a UV LED configured to radiate ultraviolet rays to the air flow passage, and a photocatalyst activated by ultraviolet rays and configured to generate materials for removing harmful components included in air. The fluid purification device may include an air purification unit used in a home, an office, a fitting shop, and a vehicle.

Other storage boxes include interior spaces for keeping articles and may include furniture or a cabinet for keeping bedclothes or clothes, for example.

Although a preferred embodiment of the present invention has been described for illustrative purposes, those skilled in the art will appreciate that various modifications, additions and substitutions are possible, without departing from the scope and the spirit of the invention as disclosed in the accompanying claims.

INDUSTRIAL APPLICABILITY

The present invention relates to a multifunction Light-Emitting Diode (LED) lighting apparatus, and more particularly, to a multifunction LED lighting apparatus which is capable of increasing the internal volume of an application on which the lighting apparatus is mounted by improving a structure in which a lighting apparatus having a sterilization and deodorization function is installed and of providing a high sterilization and deodorization function as an indoor lighting apparatus.

The invention claimed is:
1. A multifunction Light-Emitting Diode (LED) lighting apparatus installed on a product, including:
 a module including a substrate having a first surface and a second surface opposite to the first surface;
 at least one lighting LED disposed on the first surface of the substrate;

at least one ultraviolet (UV) LED disposed on the first surface of the substrate; and a cover disposed to face the substrate at a specific interval from the substrate and configured to cover the at least one lighting LED and the at least one UV LED, wherein the at least one lighting LED and the at least one UV LED are integrally disposed over the substrate to form the module, wherein the module is disposed on the product such that the second surface of the substrate is installed on an inside wall of the product, wherein the module is configured to radiate ultraviolet rays to a fluid in an interior of the product and provide illumination to the interior of the product, and wherein the cover includes a first region facing the at least one lighting LED and a second region facing the at least one UV LED, wherein the cover further includes a light diffusion unit formed in the first region and configured to diffuse light emitted from the lighting LED, wherein the cover further includes an opening unit formed in the second region such that UV rays radiated from the light UV LED are directed to the product and the cover further includes a material covering the opening unit and having a property to allow the UV rays to pass through the material, and wherein the cover further includes a partition that partitions the first region and the second region.

2. The multifunction LED lighting apparatus of claim 1, wherein the module is configured for insertion into a groove formed in the inside wall of the product.

3. The multifunction LED lighting apparatus of claim 1, wherein the opening unit is configured to expose the UV LED through the cover.

4. The multifunction LED lighting apparatus of claim 1, wherein the material includes a quartz member or a reinforced glass member.

5. The multifunction LED lighting apparatus of claim 1, wherein the material includes a metal mesh coated with a photocatalyst.

6. The multifunction LED lighting apparatus of claim 1, wherein the cover comprises:

an intake port configured to receive a supply a fluid;
a channel configured to provide a passage of the fluid; and
a discharge port configured to discharge the fluid that passes through the channel.

7. The multifunction LED lighting apparatus of claim 6, further comprising a filter connected to the intake port.

8. The multifunction LED lighting apparatus of claim 6, further comprising a fan connected to at least one of the intake port and the discharge port.

9. The multifunction LED lighting apparatus of claim 6, wherein the cover further comprises a photocatalyst coated on an inner surface of the channel.

10. The multifunction LED lighting apparatus of claim 1, wherein the UV LED comprises:

a first UV LED disposed on a first surface of the substrate; and
a second UV LED disposed on a second surface of the substrate that faces the first surface.

11. The multifunction LED lighting apparatus of claim 10, wherein:

at least one of the first UV LED and the second UV LED is configured to radiate ultraviolet rays to the inside wall of the product.

12. The multifunction LED lighting apparatus of claim 10, further comprising a housing configured to cover at least one of the first UV LED and the second UV LED.

13. The multifunction LED lighting apparatus of claim 12, further comprising a filter connected to the intake port.

14. The multifunction LED lighting apparatus of claim 12, further comprising a fan connected to at least any one of the intake port or the discharge port.

15. The multifunction LED lighting apparatus of claim 12, further comprising a photocatalyst.

16. The multifunction LED lighting apparatus of claim 1, wherein the cover and the module are configured for installation on an inside wall of the product including a home refrigerator, a vehicle freezer, a warehouse refrigerator, a cup sterilizer, a toothbrush sterilizer, a shoe sterilization deodorizer, a fluid purification device, or a storage box.

17. The multifunction LED lighting apparatus of claim 16, further comprising:

a switch configured to turn on or off in response to an operation of the product; and
a driving unit connected to the switch and configured to selectively drive the lighting LED and the UV LED in response to the on state and off state of the switch.

18. The multifunction LED light apparatus of claim 1, further comprising at least one additional UV LEDs disposed on the second surface of the substrate along the lengthwise direction of the substrate.

19. The multifunction LED light apparatus of claim 18, wherein the module is located in a groove of an inside wall of the product and the at least one additional UV LEDs are disposed to radiate UV rays toward the inside wall of the product.

* * * * *